United States Patent [19]

Shiragami et al.

[11] Patent Number: 5,942,617
[45] Date of Patent: Aug. 24, 1999

[54] PROCESS FOR PRODUCING PURINE DERIVATIVES

[75] Inventors: Hiroshi Shiragami; Yumiko Uchida; Kunisuke Izawa; Keizo Yamashita; Satoshi Katayama, all of Kawasaki, Japan

[73] Assignee: Ajinomoto Co., Inc., Tokyo, Japan

[21] Appl. No.: 08/926,471

[22] Filed: Sep. 10, 1997

[30] Foreign Application Priority Data

Sep. 10, 1996 [JP] Japan .................................. 8-239031
Oct. 24, 1996 [JP] Japan .................................. 8-282216

[51] Int. Cl.$^6$ ...................... C07D 473/18; C07D 473/34; C07D 473/30; C07D 473/16
[52] U.S. Cl. .......................... 544/276; 544/230; 544/265; 544/267; 544/271; 544/272; 544/273; 544/277
[58] Field of Search ...................... 544/265, 267, 544/230, 271, 272, 273, 276, 277

[56] References Cited

U.S. PATENT DOCUMENTS

| 5,310,895 | 5/1994 | Shiragami et al. | 536/27.14 |
|---|---|---|---|
| 5,336,770 | 8/1994 | Shiragami et al. | 544/276 |
| 5,466,793 | 11/1995 | Honda et al. | 536/55.3 |
| 5,625,057 | 4/1997 | Shiragami et al. | 536/55.3 |
| 5,633,366 | 5/1997 | Takamatsu et al. | 536/28.4 |
| 5,688,948 | 11/1997 | Izawa et al. | 544/276 |

FOREIGN PATENT DOCUMENTS

| 0 728 757 | 6/1986 | European Pat. Off. . |
|---|---|---|
| 0 302 644 | 2/1989 | European Pat. Off. . |
| 0 352 953 | 1/1990 | European Pat. Off. . |
| 0 184 473 | 8/1996 | European Pat. Off. . |

OTHER PUBLICATIONS

Hawley's Condensed Chemical Dictionary, 12th edition, pp. 21–22, 1990.
Brookes et al J. Chem. Soc. (C), 1968, pp. 2026–2028.
Er–Rhaimini Synthesis, 1988, pp. 154–155.
Piper, J. Med. Chem. 23, 357, 1980.

*Primary Examiner*—Mark L. Berch
*Attorney, Agent, or Firm*—Oblon, Spivak McClelland, Maier & Neustadt, P.C.

[57] ABSTRACT

A process for preparing 7-benzylpurine derivatives is provided. An acetylpurine nucleoside is reacted with a benzyl halide to benzylate the 7-position of the purine base, and an acid is then added to the reaction mixture to hydrolyze the glycoside bond. The 7-benzylpurines may be used to prepare 9-substituted purine derivatives.

20 Claims, No Drawings

PROCESS FOR PRODUCING PURINE DERIVATIVES

BACKGROUND OF THE INVENTION

1. Field of the Invention

The present invention relates to a process for producing purine derivatives having antiviral activity and antitumor activity which are useful as pharmaceuticals. More specifically, the present invention relates to a process for producing 7-benzylpurine derivatives, and a process for producing purine derivatives by a selective addition reaction at the 9-position of the 7-benzylpurine derivatives.

2. Discussion of the Background

Nucleoside derivatives which inhibit viral replication are important agents for treating a variety of viral diseases, such as herpes, AIDS, hepatitis, cytomegalovirus, for example. Purine derivatives having a substituent at the 9-position of the purine base are well-known to have antiviral activity, including already approved medications such as acyclovir, ganciclovir, penciclovir, famciclovir and the like, as well as other derivatives which are currently under development.

These purine derivatives are usually produced by a method in which a substituent called a side chain is added to a purine base. It is very difficult to introduce a substituent only at the desired 9-position of a purine base, and a substituent may also be introduced at the 7-position in addition to the desired 9-position. Thus, it was necessary to conduct isomerization after the addition reaction, and a step of removing by-products was required.

Known examples thereof include a method in which guanine or N-acetylguanine is used as a starting material in the synthesis of penciclovir [Chinese J. of Chem., 9, 536, 1991], a method in which 2-amino-6-chloropurine is reacted with a brominated side chain [Tetrahedron Lett. 26(35) 4265, 1985], and a method in which 2-amino-6-benzyloxypurine is reacted with tosylate as a side chain [J. Heterocyclic Chem. 26(5), 1261, 1989]. However, all of these methods require an intricate purification step.

Further, a method in which 2-amino-6-chloropurine is reacted with an iodinated side chain in the synthesis of famciclovir [Tetrahedron Lett. 46(19), 6903, 1990], and a method in which 2-amino-6-chloropurine is subjected to the Michael addition reaction with a side chain precursor [Tetrahedron Lett. 33(32) 4609, 1992] are known with respect to the synthesis of famciclovir. These methods, however, also require an intricate treatment step.

In the above-mentioned documents, the side chain portion is generally introduced as an alkyl halide. Besides, a desired compound is formed by addition-reacting a cyclopropanedicarboxylic acid compound with 2-amino-6-chloropurine using potassium carbonate as a base [Nucleosides & Nucleotides, 15(5), 981, 1996]. Nevertheless, in this method as well, the yield of the desired 9-position addition produce is as low as 60%, and the 7-position addition product as a by-product is formed in a large amount (34%). Thus, the isomerizing step was required in this method as well.

At any rate, in these reactions, the amino proton of the secondary amine in the 9-position of the purine is eliminated with the addition of a base, an anion is formed in the amine group, and the reaction with the side chain portion is conducted therein.

As a method to solve this problem the present inventors found that the addition reaction selectively proceeds in the 9-position by reacting 7-benzylpurine derivatives represented by formula (2):

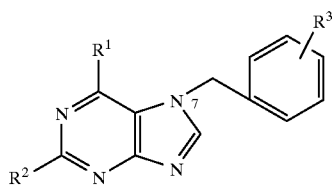

where
R$^1$ represents a hydrogen atom, a hydroxyl group, a C$_1$–C$_8$ saturated or unsaturated lower alkoxy group, a C$_1$–C$_8$ saturated or unsaturated lower acyloxy group, a siloxy group, a fluorine atom, a chlorine atom, a bromine atom, an iodine atom, an amino group, an amino group protected with one or two protective groups selected from a C$_1$–C$_8$ acyl group, a C$_1$–C$_8$ alkoxycarbonyl group and an aryloxycarbonylamino group, or a C$_1$–C$_8$ saturated or unsaturated lower alkyl group, R$^2$ represents a hydrogen atom, a hydroxyl group, a C$_1$–C$_8$ saturated or unsaturated lower alkoxy group, a C$_1$–C$_8$ saturated or unsaturated lower acyloxy group, a siloxy group, a fluorine atom, a chlorine atom, a bromine atom, an iodine atom, an amino group, an amino group protected with one or two protective groups selected from a C$_1$–C$_8$ acyl group, a C$_1$–C$_8$ alkoxycarbonyl group and an aryloxycarbonylamino group, or a C$_1$–C$_8$ saturated or unsaturated lower alkyl group, and R$^3$ represents a hydrogen atom, a C$_1$–C$_6$ lower alkyl group, a C$_1$–C$_6$ lower alkoxy group, a hydroxyl group, a nitro group, an amino group, a sulfonic acid group, a carboxy group, a C$_1$–C$_6$ alkoxycarbonyl group, a fluorine atom, a chlorine atom, a bromine atom, or an iodine atom, with an alkyl halide-type side chain under neutral conditions, as required, by heating. Further, it was found that purine derivatives can be formed in which the desired substituent is introduced into the 9-position alone by debenzylating the resulting compound (Japanese Patent Application No. 10,710/1996).

The above-mentioned method can be used to selectively produce purine derivatives having a substituent in the 9-position which exhibit antiviral activity, and may be used on an industrial scale.

The following methods have been employed to produce the 7-benzylpyrine derivatives which are used as a starting material in the above-mentioned method.

1. A method in which 7-benzylguanine is produced by reacting guanosine with benzyl bromide in a dimethyl sulfoxide solvent, and then treating the reaction mixture with an acid [J. Chem. Soc. (C) 2026, 1968; Synthetic Commun., 20(16), 2459, 1990].
2. A method in which 7-benzylhypoxanthine is formed by reacting inosine with benzyl bromide in a dimethyl sulfoxide solvent, and then treating the reaction mixture with an acid (J. Heterocyclic Chem., 25, 1179, 1988).
3. A method in which 7-benzyladenine is formed from adenine through three steps (Synthesis 154, 1988).

These methods can produce the desired 7-benzylpurine derivatives of formula (2) without any trouble on a laboratory scale where approximately 1 g of the product is produced. However, since a hydroxyl group of the sugar moiety of guanosine is also benzylated in the above-mentioned method, a large amount of benzyl bromide is required. Even when using a large amount of benzyl bromide, the yield is only approximately 80%. Thus, these methods were not satisfactory. Further, a process in which dimethyl sulfoxide, which has a possibility of run-away or explosion during the mixing with a halogenated substance, is used as a solvent and a bromide is added thereto was not appropriate in a method for producing more than 1 kg of a product on an industrial scale. Further, dimethyl sulfoxide has a high boiling point and is expensive. Thus, the above-mentioned methods are not suitable on an industrial scale.

Under these circumstances, the present inventors first tried to conduct the reaction in the absence of a solvent or to change the solvent from dimethyl sulfoxide to other solvents. They conducted investigations upon using dimethylformamide, dimethylacetamide, acetonitrile, N-methylpyrrolidinone or the like as a solvent. However, the benzylation did not proceed well, even with heating, and the desired 7-benzylpurine derivatives of formula (2) were obtained in a low yield of 10% or less, or were not obtained at all.

Meanwhile, it is known that the above-mentioned cyclopropanedicarboxylic acid compound reacts with a primary amine such as aniline [J. Am. Chem. Soc., 97(11), 3239, 1975], lysine derivatives (J. Org. Chem., 50, 3631, 1985) or hydrazine derivatives [Heterocycles, 36(2), 219, 1993)]. It is further known that the above-mentioned compound reacts with a secondary amine such as piperidine to form zwitter ions, and that it reacts with a weakly nucleophilic tertiary amine such as pyridine to form the same ionic compound [J. Am. Chem. Soc., 97(11), 3239, 1975].

With respect to the reaction of an amine having a structure similar to that of 7-benzylguanine (purine) with a cyclopropanedicarboxylic acid compound, the reaction of imidazole derivatives, pyrrole derivatives or purine derivatives is known. However, a base was required in this reaction (J. Org. Chem., 47, 1682, 1982, Hisamitsu Pharmaceuticals; JP 87-227702).

Thus, in the reaction of the cyclopropanedicarboxylic acid compound, the addition reaction under basic conditions is only known for compounds having two or more nitrogen atoms in the ring, such as purine base derivatives. The reaction under neutral conditions was not known at all. The addition reaction at the tertiary nitrogen atom of the purine base derivatives was not known, either.

SUMMARY OF THE INVENTION

It is an object of the present invention to provide a process for preparing 7-benzylpurine derivatives which is safe and provides high yields of the desired compounds and does not require dimethyl sulfoxide as a solvent or a large amount of benzylating agent.

It is another object of the present invention to provide a process for selectively producing compounds having a side chain at the 9-position of purine base.

The present inventors considered that a purine nucleoside in which the hydroxyl groups of the sugar moiety are protected may have a higher solubility in a solvent than the nucleotide per se, and that a solvent other than dimethyl sulfoxide may be used, and the amount of a benzylating agent may be decreased.

The inventors have discovered that an acetyl-protected purine nucleoside may be reacted with a benzyl halide in the absence of a solvent or in the presence of an industrially available solvent other than dimethyl sulfoxide, and after the completion of the benzylation, an acid may be directly added to the reaction solution to hydrolyze the glycosidic bond, whereby 7-benzylpurine derivatives may be formed in a high yield. These findings have led to the completion of the present invention.

The objects described above, and others, are accomplished with a process for producing 7-benzylpurine derivatives represented by formula (2):

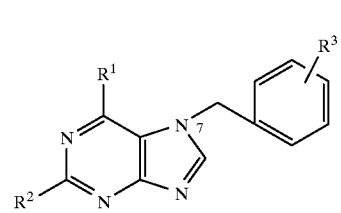

(2)

where
$R^1$ represents hydrogen, a hydroxyl group, a $C_1$–$C_8$ saturated or unsaturated lower alkoxy group, $C_1$–$C_8$ a saturated or unsaturated lower acyloxy group of a siloxy group, a fluorine atom, a chlorine atom, a bromine atom, an iodine atom, an amino group, an amino group protected with one or two $C_1$–$C_8$ acyl groups, a $C_1$–$C_{10}$ alkoxycarbonylamino group, an aryloxycarbonylamino group, an optionally substituted benzyloxycarbonylamino group, or a $C_1$–$C_8$ saturated or unsaturated lower alkyl group, $R^2$ represents hydrogen, a hydroxyl group, a $C_1$–$C_8$ saturated or unsaturated lower alkoxy group, a $C_1$–$C_8$ saturated or unsaturated lower acyloxy group, a siloxy group, a fluorine atom, a chlorine atom, a bromine atom, an iodine atom, an amino group, an amino group protected with one or two $C_1$–$C_8$ acyl groups, a $C_1$–$C_{10}$ alkoxycarbonylamino group, an aryloxycarbonylamino group, an optionally substituted benzyloxycarbonylamino group, or a $C_1$–$C_8$ saturated or unsaturated lower alkyl group, and $R^3$ represents hydrogen, a $C_1$–$C_6$ lower alkyl group, a $C_1$–$C_6$ lower alkoxy group, a hydroxyl group, a nitro group, an amino group, a sulfonic acid group, a carboxy group, a $C_1$–$C_6$ alkoxycarbonyl group, a fluorine atom, a chlorine atom, a bromine atom, or an iodine atom, which comprises adding an unsubstituted or substituted benzyl halide to an acetylpurine nucleoside represented by formula (1):

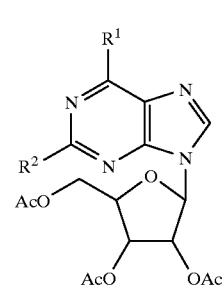

(1)

where
$R^1$ and $R^2$ are as defined above, to benzylate the 7-position of the purine, followed by hydrolyzing the glycosidic bond with an acid.

Further, the present inventors have conducted tests for reactivity of 7-benzylpurine derivatives with various side chains other than an alkyl halide. Consequently, they have found, surprisingly, that a cyclopropanedicarboxylic acid compound reacts well with 7-benzylpurine derivatives of formula (2) in the presence or absence of a solvent under neutral conditions without using a base and without adding a catalyst or other reagents to give a zwitter ion-type addition compound in a high yield.

Thus, the objects of the present invention are also accomplished with a process for producing a compound represented by formula (5):

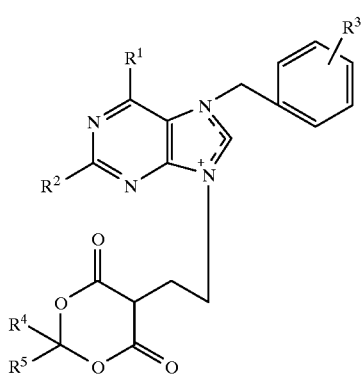

(5)

where $R^1$, $R^2$ and $R^3$ are as defined above; and $R^4$ and $R^5$, which may be the same or different, each represent a hydrogen atom, a $C_1$–$C_{20}$ linear or branched saturated or unsaturated alkyl group, a $C_1$–$C_{20}$ alkoxy group, a $C_1$–$C_{20}$ acyl group, a $C_1$–$C_{10}$ acyloxy group, a carboxyl group or a $C_1$–$C_{10}$ alkoxycarbonyl group, or $R^4$ and $R^5$ may, together with the carbon atom they are bonded to, form a 3- to 8-membered ring, which comprises reacting the 7-benzylpurine derivative represented by formula (2):

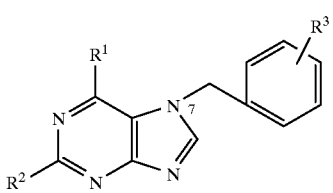

(2)

where $R^1$, $R^2$ and $R^3$ are as defined above, with a cyclopropanecarboxylic acid compound represented by formula (4):

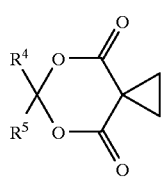

(4)

where $R^4$ and $R^5$ are as defined above.

The objects of the present invention are also accomplished with a process for producing a 9-substituted purine derivative represented by formula (6):

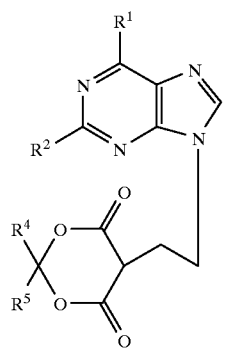

(6)

where $R^1$, $R^2$, $R^4$ and $R^5$ are as defined above, which comprises debenzylating the compound represented by formula (5).

In a preferred embodiment, the compound of formula (5) may be converted into the 9-substituted purine derivative of formula (6) by debenzylation without isolatation.

In a preferred embodiment of the present invention, when, in formula (2), $R^1$ is a hydroxyl group, $R^2$ is an amino group, a $C_1$–$C_8$ mono- or diacylamino group, a $C_1$–$C_8$ alkoxycarbonylamino group or an aryloxycarbonylamino group and $R^4$ and $R^5$ of the compound of formula (4) are methyl groups, a compound represented by formula (7):

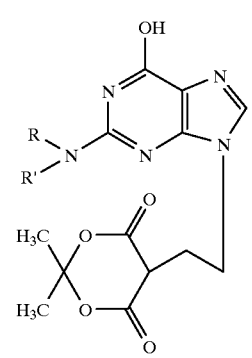

(7)

is produced by the addition and debenzylation reactions. This compound may be converted to penciclovir derivatives represented by formula (8) or famciclovir derivatives represented by formula (9) by, for example, the method of Graham R. Geen et al, see Nucleosides & Nucleotides, 15(5), 981, 1996, incorporated herein by reference.

(8)

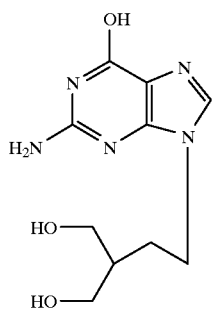

(9)

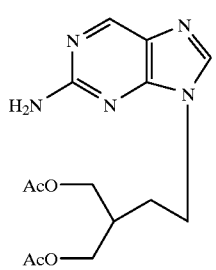

DETAILED DESCRIPTION OF THE INVENTION

The present invention provides for the industrial production of 7-benzylpurine derivatives which are valuable as pharmaceuticals and also provides for the selective production of purine derivatives having a substituent in the 9-position which are also useful as pharmaceuticals.

In the present invention, $R^1$ and/or $R^2$ may be a siloxy group. Preferably, this group is a trialkyl siloxy group, where the alkyl groups have 1 to 8 carbon atoms.

$R^1$ and/or $R^2$ may be a unsubstituted or a substituted benzyloxycarbonyl amino group. Suitable substituents in the benzyloxycarbonylamino group include a $C_1$–$C_8$ saturated or unsaturated alkyl group, a $C_1$–$C_8$ alkoxy group and a halogen atom (e.g., fluorine, chlorine, bromine or iodine). In a preferred embodiment, the benzyloxycarbonyl amino group has one substituent.

$R^1$ and/or $R^2$ may be an aryloxycarbonylamino group. The aryl moiety may have 6 to 15 carbon atoms. In preferred embodiment, the aryl moiety is a phenyl group. The aryl moiety may have substituents (i.e., the aryloxycarbonylamino group is substituted or unsubstituted). Suitable substituents include those discussed for the benzyloxycarbonylamino group, above. Preferably, the aryl moiety has one substituent.

$R^4$ and $R^5$ may, together with the carbon atom they are bonded to, form a 3- to 8-membered ring. In a preferred embodiment, the ring members are all carbon atoms. In a particularly preferred embodiment, $R^4$ and $R^5$ together form a cyclic alkyl group having 3 to 8 carbon atoms. Suitable examples of such groups include cyclopropyl groups, cyclobutyl groups, cyclopentyl groups, cyclohexyl groups, cycloheptyl groups and cyclooctyl groups. The ring formed by $R^4$, $R^5$ and the carbon atom they are bonded to may also contain one or more heteroatoms, such as one, two or three heteroatoms. One or two heteroatoms is preferred. Suitable heteroatoms include nitrogen, oxygen and sulfur. One particularly preferred example of a cyclic ring containing hetroatoms is a —CH$_2$—O—CH$_2$—O—CH$_2$— group, where — represents a bond to the carbon atom to which $R^4$ and $R^5$ are bonded in formulae (4)–(7).

The acetylpurine nucleoside of formula (1) used in the present invention may be prepared by acetylating a purine nucleoside according to well-known methods. Examples of the purine nucleoside include those which are obtained industrially through fermentation or the like. Examples thereof include guanosine, adenosine, inosine, xanthine and 9-(β-D-ribofuranosyl)-2-aminopurine. The purine base may be partially substituted, and its alkali salt may also be used. As the alkali salt, the sodium salt is particularly preferred. The potassium salt or an ammonium salt are also suitable.

The acetyl protection may be conducted by directly adding from 3 to 10 equivalents of acetic anhydride to an alkali salt of a purine nucleoside. Alternatively, the reaction may be conducted by adding from 3 to 10 equivalents of acetic anhydride to a purine nucleoside in the presence of a base such as pyridine, triethylamine or the like. When acetic anhydride is used in an amount of from 5 to 6 equivalents, the reaction yields are high. In order to improve the slurry property of the reaction solution, acetic acid may be used in an appropriate amount. Further, an inert solvent that does not directly participate in the reaction may also be used. However, when the solubility of the starting material is low, the yield may decrease. The reaction may be conducted at a reaction temperature of from room temperature to approximately the boiling point of acetic anhydride. In the case of the sodium salt, an exothermic reaction usually occurs, and is completed within a short period of time. A reaction time of from 30 minutes to 1 hour is usually sufficient, and the acetylation can also be completed by continuing the heating.

When guanosine is used as a starting material in the acetylation, the base moiety (guanine) has an amino group, and the reaction product is, therefore, tetraacetylguanosine which is a tetraacetyl compound. This compound is also included within the scope of the acetylpurine nucleoside used in the present invention.

The benzyl halide may be directly added to the triacetylpurine nucleoside solution obtained by the abovementioned method, and the mixture can be heated to conduct the benzylation, whereby a 7-benzylpurine derivative is obtained. Further, the 7-benzylpurine derivative may also formed by reacting the isolated acetylpurine nucleoside with the benzyl halide in the absence or presence of a solvent.

Examples of the benzyl halide used include benzyl chloride, benzyl bromide, benzyl iodide and p-nitrobenzyl bromide. They may be used either singly or in combination. Further, the benzene ring may have a substituent. Examples of suitable substituents include a lower alkyl group such as a methyl group or an ethyl group, a lower alkoxy group such as a methoxy group, a hydroxyl group, a nitro group, an amino group, a sulfonic acid group, a carboxy group, an alkoxycarbonyl, group such as a methoxycarbonyl group, a fluorine atom, a chlorine atom, a bromine atom, and an iodine atom. In a preferred embodiment, the benzyl halide is represented by formula (10):

(10)

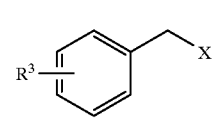

where

X is a halogen atom and $R^3$ is defined above. Preferably, X is a fluorine, chlorine, bromine or iodine atom, and, more preferably, a chlorine, bromine or iodine atom.

The amount of benzyl halide used in the reaction may vary widely. The amount of benzyl halide used maybe between 1 and 5 equivalents, based on the acetylpurine nucleoside. Especially when it is used in an amount of from 2 to 3 equivalents, the reaction proceeds efficiently to provide a good yield. Further, approximately 10 equivalents thereof can also be used without the use of the solvent. In order to complete the reaction, the heating is usually conducted at a temperature of from 30° C. to 100° C. Especially, the range of from 50° to 70° is preferable. The reaction is conducted until the starting material disappears, and is completed in from 10 to 100 hours, usually in from 12 to 24 hours. These time ranges include all specific values and subranges therebetween.

After the completion of the reaction, an acid maybe directly added to the reaction solution to hydrolyze the glycosidic bond. Hydrochloric acid or sulfuric acid is particularly preferred. The amount of the acid used is usually between 5 and 50 equivalents, preferably between 10 and 20 equivalents. When the acid is added, heat maybe generated spontaneously. The acid is added with cooling as required. After the dropwise addition of the acid, the reaction is almost completed in from 30 minutes to 1 hour. In order to complete the hydrolysis, it is also possible that after the heat generation is finished, the heating is conducted at 50° C. for from 1 to 5 hours. As the hydrolysis proceeds, the 7-benzylpurine derivatives may precipitate as crystals. Accordingly, the compound of formula (2) may be produced as a salt of the acid used to hydrolyze the glycosidic bond.

After the completion of the hydrolysis, the reaction solution maybe crystallized with the addition of a crystallization solvent. Preferable examples of the crystallization solvent include alcohols, such as methanol, ethanol and 2-propanol. A mixed solvent of alcohol and water and other organic solvents may also be used depending on the substrate to be crystallized. The amount of the solvent is between 1 and 20 times as large as that of the reaction solution. It is usually between 2 and 5 times. The solvent is added dropwise at room temperature while being stirred. It is also possible that the addition is conducted at a relatively high temperature, and the reaction mixture is then cooled and crystallized. After the solvent is added dropwise, the mixture may be cooled to room temperature or to approximately 0° C., and stirred for from 30 minutes to 1 hour to separate the crystals. The crystals are usually washed with a crystallization solvent, and then dried. In this manner, 7-benzylpurine derivatives such as 7-benzylguanine, 7-benzyladenine, 7-benzylhypoxanthine, 7-benzyl-2-aminopurine, 7-benzylxanthine or these compounds in which the position other than the 7-position is substituted are isolated as crystals.

The compound of formula (4) may be prepared by the method described in Org. Synth. 60, 66, 1981 or J. Org. Chem., 40 (20) 2969, 1975, both incorporated herein by reference. This compound is usually prepared by reacting bromoethane with a malonic acid derivative to form 1,1-cyclopropanedicarboxylic acid, and then cyclizing the carboxylic acid to conduct the protection.

The compound of formula (5), which is a desired compound of the present invention, may be obtained by reacting the compound of formula (2) with the compound of formula (4).

The compound of formula (2) may be used as the free base or of a salt thereof, such as a hydrochloride or a sulfate. Further, the amino group in a purine base may be protected with a protective group which is ordinarily used in the synthesis of nucleic acids, such as an acyl group. Suitable acyl groups may have 1 to 15 carbon atoms.

The reaction may be conducted in the presence or absence of a solvent. Examples of the solvent include dimethyl sulfoxide; N,N-dimethylformamide; N,N-dimethylacetamide; N-methylpyrrolidinone; aromatic hydrocarbons (such as toluene and xylene); ethers (such as diethyl ether, diisopropyl ether and dioxane); alcohols (such as methanol, ethanol and isopropyl alcohol); esters (such as ethyl acetate, methyl acetate and isobutyl acetate); nitriles (such as acetonitrile); and ketones (such as acetone, methyl ethyl ketone and methyl isobutyl ketone); and halogen-type solvents (such as chloroform and dichloromethane). They may be used either singly or in combination. In view of the solubility of the purine base, the reaction proceeds well, in many cases, with dimethyl sulfoxide, N,N-dimethylformamide, N,N-dimethylacetamide or N-methylpyrrolidinone. Further, the reaction in the absence of the solvent is not problematic.

The reaction is conducted usually at from 0 to 200° C., preferably at from 10 to 100° C. The reaction is usually completed in from 0.5 to 48 hours. The concentration of the reactants is usually 0.1 g/dL or more, or the reaction is conducted in the absence of the solvent. Preferably, the concentration is approximately 1 g/dL. A molar ratio of (2) to (4) in the reaction is usually 1:1. In order to increase the yield, it is also possible to use one or the other in a larger amount.

In the present invention, since the 7-benzylpurine derivative is used as a starting material, only the 9-position addition product is obtained in a high yield exceeding 90%, and no 7-position addition product is formed at all.

The compound of formula (5) obtained in the present reaction is a novel compound, and it is an important intermediate for the production of the desired compound which has the substituent in the 9-position of the purine. Further, it is a compound which can easily be synthesized for the first time by the process of the present invention.

The compound of formula (5) is a compound in which zwitter ions are formed in the molecule. It is generally considered to have the structure of formula (5), but it may have a structure represented by formula (5').

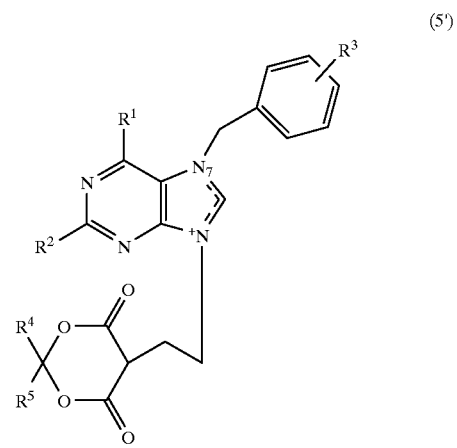

(5')

Since the compound of formula (5) generally has a very low solubility in the reaction solvent, it can usually be isolated easily by filtering the compound precipitated outside the reaction system as the above-mentioned reaction proceeds. To improve the slurry property of the solution, a solvent such as ethyl acetate or chloroform may be added.

The desired compound of formula (6) may be formed by debenzylating the compound of formula (5) to eliminate the benzyl group or the substituted benzyl group. The reaction may be conducted in the presence of a solvent using the compound of formula (5) isolated above. Or, the reaction solution from which the compound of formula (5) has been formed can be debenzylated as such or with the addition of a solvent.

In the compound of formula (5), the benzyl group or the p-nitro benzyl group in the 7-position may be eliminated by a general method of removing an N-benzyl group, for example, by reduction in a hydrogen atmosphere in the presence of a palladium catalyst, by reduction with a palladium catalyst in the presence of formic acid or a formic acid salt, or by reduction using sodium and ammonium.

Examples of the palladium catalyst include palladium on carbon, palladium hydroxide, palladium black, a Lindlar catalyst, Pd—$CaCO_3$ and Pd—$BaCO_3$. The amount of the catalyst is usually between 1 and 10-mol % based on the substrate.

Hydrogen to be used may be reacted at a normal pressure. The reaction rate can be increased under increased pressure. The reaction is usually conducted at a pressure of from 1 to 5 atm.

In the case of a substituted benzyl group which can be eliminated under acidic conditions or with light, such as a 3,4-dimethoxybenzyl group, an o-nitrobenzyl group or a di-(p-methoxyphenyl)methyl group, the elimination is conducted by the corresponding method.

Examples of the solvent include water; N,N-dimethylformamide; N,N-dimethylacetamide; N-methylpyrrolidinone; aromatic hydrocarbons (such as toluene and xylene); ethers (such as diethyl ether, diisopropyl ether and dioxane); alcohols (such as methanol, ethanol and isopropyl alcohol); carboxylic acids (such as acetic acid and propionic acid); esters (such as ethyl acetate, methyl acetate and isobutyl acetate); nitrites (such as acetonitrile); and ketones (such as acetone, methyl ethyl ketone and methyl isobutyl ketone). They are used either singly or in combination. The reaction proceeds well, in many cases, with N,N-dimethylformamide, N,N-dimethylacetamide, N-methylpyrrolidinone, carboxylic acids (such as acetic acid and propionic acid), and alcohols (such as methanol, ethanol and isopropyl alcohol) due to their solubizing properties.

The reaction is usually conducted at from 0 to 150° C., preferably at from 10 to 80° C. The reaction is usually completed in from 0.5 to 48 hours. The reaction concentration is usually between 1 and 10 g/dL.

After the completion of the reaction, the catalyst is filtered off, the solvent is concentrated as required, a poor solvent is added or extraction is conducted, whereby the desired product may be isolated.

Having generally described this invention, a further understanding can be obtained by reference to certain specific examples which are provided herein for purposes of illustration only and are not intended to be limiting unless otherwise specified.

EXAMPLES

Example 1

Production of Triacetylguanosine

Acetic anhydride (12.7 ml, 4.5 equivalents) was added to 9.19 g (30.0 mmols) of guanosine sodium salt (molecular weight 306.23), and the mixture was stirred at room temperature. Approximately 10 minutes later, the temperature inside the system was elevated to 100° C., and the reaction solution was dissolved uniformly. Then, the temperature was gradually decreased to form a slurry. Subsequently, the reaction was conducted at 60° C. for 2 hours. During this reaction, 5 ml of acetic acid were added to improve the stirrability. After it was identified through liquid chromatography that the starting material disappeared, the temperature was returned to room temperature, and the reaction solution was concentrated, and evaporated to dryness. To the residue were added 30 ml of acetonitrile. The mixture in the slurry state was stirred for 1 hour, and then filtered. The solid was washed twice with 5 ml of acetonitrile, then dried at 50° C. under reduced pressure, and analyzed. As a result, it was found that the resulting solid was almost a salt (triacetylguanosine 0.7% by weight). The mother liquor contained 23.6% of triacetylguanosine which corresponded to a yield of 97.6%. The formation of 7-benzylguanine was conducted using this solution.

Triacetylguanosine was isolated in the following manner. The mother liquor was concentrated, and water was added to the resulting residue. The mixture was neutralized with a 1-N sodium hydroxide aqueous solution while being stirred. When the semi-transparent slurry solution was heated at approximately 90° C., it was instantaneously dissolved, but soon a large amount of a white solid was precipitated. The temperature was returned to room temperature, and the slurry was stirred overnight, and then filtered. The crystals were washed three times with 20 ml of water, and dried at 50° C. under reduced pressure for 5 hours to give 11.66 g of triacetylguanosine crystals in a crystallization yield of 98.1%.

1H NMR (DMSO-d6): d 10.73 (s, 1H, NH), 7.92 (s, 1H, H-8), 6.53 (s, 2H, NH2), 5.98 (d, 1H, H-1'), 5.78 (t, 1H, H-2'), 5.48 (dd, 1H, H-3'), 4.30 (m, 3H, H-5', H-4'), 2.10 (s, 3H, CH3), 2.04 (s, 3H, CH3), 2.03 (s, 3H, CH3); FAB-MS (MH+)=410.3.

Example 2

Production of 7-Benzylguanine Dihydrochloride

Benzyl bromide (0.73 ml, 2.50 equivalents) was added to 4.24 g of an acetonitrile solution containing 1.0 g (corresponding to 2.45 mmols) of triacetylguanosine obtained in Example 1, and the mixture was stirred at 60° C. for 19 hours. The temperature was returned to room temperature, and 2.1 ml (10 equivalents) of conc. hydrochloric acid were added thereto. The mixture was reacted for 2 hours. The solid was precipitated in 1.5 hours. Ten milliliters of methanol were added thereto, and the slurry was stirred for 2 hours, and then filtered. The crystals were washed twice with 5 ml of methanol, and dried at 55° C. under reduced pressure for 3 hours to give 0.61 g of 7-benzylguanine in a yield of 79.2%.

1H-NMR (DMSO-d6): d 8.87 (s, 1H, H-8), 7.35 (m, 5H, C6H5), 5.52 (s, 2H, CH2); FAB-MS (MH+)=242.2.

Example 3

Production of 7-Benzylguanine Dihydrochloride

Benzyl chloride (2.14 ml, 10.0 equivalents) was added to 3.21 g of an acetonitrile solution containing 0.76 g (corresponding to 1.86 mmols) of triacetylguanosine obtained in Example 1, and the mixture was reacted at 70° C. for 71 hours. The temperature was returned to room temperature, and 3.13 ml (20 equivalents) of conc. hydrochloric acid were added thereto. When the mixture was reacted for 3 hours, the solid was precipitated. Ten milliliters of methanol were added thereto, and the slurry was stirred

Example 4

Production of 7-Benzylguanine Dihydrochloride

Four milliliters of acetonitrile and 0.59 ml (2.7 equivalents) of benzyl bromide were added to 0.755 g (1.84 mmols) of triacetylguanosine, and the mixture was reacted at 50° C. for 16 hours. Subsequently, 2.5 ml (16.1 equivalents) of conc. hydrochloric acid were added thereto. The reaction was conducted at 50° C. for 50 minutes, and the temperature was then returned to room temperature. Then, the solid was precipitated. Fifteen milliliters of methanol were added thereto, and the slurry was stirred for 1 hour, and then filtered. The crystals were washed twice with 5 ml of methanol, and dried at 50° C. under reduced pressure for 2 hours to give 0.496 g of 7-benzylguanine crystals in a yield of 85.8%.

Example 5

Production of 7-Benzylguanine Dihydrochloride

Triacetylguanosine (0.756 g, 1.85 mmols) was suspended in 6 ml of acetonitrile, and 0.28 ml (1.25 equivalents) of benzyl bromide and 0.27 ml (1.25 equivalents) of benzyl chloride were added to the suspension. The mixture was reacted at 50° C. for 24 hours and at 60° for 23 hours. The temperature was returned to room temperature, and 1.58 ml (10.1 equivalents) of conc. hydrochloric acid were added thereto. The resulting mixture was reacted for 3 hours. After 40 minutes of the reaction, the solid was precipitated. Fifteen milliliters of methanol were added thereto, and the slurry was stirred for 1.5 hours, and then filtered. The crystals were washed twice with 5 ml of methanol, and dried at 50° C. under reduced pressure for 4 hours to give 0.468 g of 7-benzylguanine crystals in a yield of 80.5%.

Example 6

Production of 7-Benzylguanine Dihydrochloride

Four milliliters of N,N-dimethylformamide and 0.53 ml (2.49 equivalents) of benzyl chloride were added to 0.758 g (1.85 mmols) of triacetylguanosine, and the reaction was conducted at 60° C. for 22 hours. It was identified through liquid chromatography that 69% of the starting material remained. Accordingly, 1.60 ml (10 equivalents in total) of benzyl chloride were further added thereto, and the reaction was conducted at 60° C. for 23 hours and at 70° C. for 5 hours. The temperature was returned to room temperature, and 1.57 ml (10 equivalents) of conc. hydrochloric acid were added to the solution. The reaction was conducted for 2 hours, but the cleavage of the sugar moiety was not completed. Therefore, 1.58 ml (20 equivalents in total) of conc. hydrochloric acid were further added, and the mixture was stirred overnight at room temperature. Ten milliliters of methanol were added to the reaction solution in the slurry state. The mixture was stirred for 2 hours, and then filtered. The crystals were washed twice with 5 ml of methanol, dried at 50° C. under reduced pressure for 5 hours to give 0.444 g of 7-benzylguanine crystals in a yield of 76.4%.

Example 7

Production of 7-Benzylguanine Dihydrochloride

Eight milliliters of acetonitrile and 2.13 ml (10 equivalents) of benzyl chloride were added to 0.758 g (1.85 mmols) of triacetylguanosine, and the mixture was reacted at 70° C. for 47 hours. The temperature was returned to room temperature, and 3.13 ml (20 equivalents) of conc. hydrochloric acid were added thereto. The reaction was conducted for 4 hours. After 2 hours of the reaction, the solid was precipitated. Ten grams of methanol were added thereto, and the slurry was stirred overnight, and then filtered. The crystals were washed twice with 5 ml of methanol, and dried at 50° C. under reduced pressure to give 0.456 g of 7-benzylguanine crystals in a yield of 78.5%.

Example 8

Production of Tetraacetylguanosine

Acetic anhydride (41.5 ml, 8.8 equivalents) was added to 15.31 g (50.01 mmols) of guanosine sodium salt, and the mixture was reacted at approximately 100° C. for 22 hours. After it was identified through liquid chromatography that the reaction was completed, the temperature was returned to room temperature, and the reaction product was concentrated. To the residue were added 100 ml of chloroform and 50 ml of a saturated sodium hydrogencarbonate aqueous solution, and the organic layer was further washed with 50 ml of a sodium hydrogencarbonate aqueous solution and with 50 ml of water. The organic layer was concentrated, and crystalized though azeotropy with isopropanol. The residue was collected, and dried at 55° C. under reduced pressure to give 22.86 g of tetraacetylguanosine crystals in a yield of 98.8%.

1H NMR (CDCl3): d 12.00 (s, 1H, NH), 9.37 (s, 1H, NH), 7.71 (s, 1H, H-8), 5.95 (d, 1H, H-1'), 5.94 (t, 1H, H-2'), 5.72 (t, 1H, H-3'), 4.65 (m, 1H, H-4'), 4.46 (m, 2H, H-5'), 2.32 (s, 3H, CH3), 2.15 (s, 3H, CH3), 2.15 (s, 3H, CH3), 2.09 (s, 3H, CH3); FAB-MS (MH+)=451.2.

Example 9

Production of 7-Benzylguanine Dihydrochloride

Tetraacetylguanosine (0.904 g, 2.00 mmols) was dissolved in 2 ml of acetonitrile, and 0.59 ml (2.48 equivalents) of benzyl bromide were added thereto. The reaction was conducted at 50° C. for 17 hours. After it was identified through HPLC that the starting material disappeared, 5 ml (29.6 equivalents) of conc. hydrochloric acid were added to the reaction solution, and the mixture was stirred at 50° C. for 3 hours. Then, the reaction solution turned black, and the gray solid was precipitated. The temperature was returned to room temperature, and 5 ml of methanol were added to the solid. The slurry was stirred for 20 minutes, and then filtered. The crystals were washed with 10 ml of methanol, and dried at 50° C. under reduced pressure to give 0.690 g of gray crystals in a yield of 57.4%.

Synthesis Example 1

Guanosine (20.1 g, 62.7 mmols, water content 11.5%) was dissolved in 100 ml of dimethyl sulfoxide, and 20 ml (166 mmols) of benzyl bromide were added dropwise thereto over a period of 20 minutes. The mixture was stirred at room temperature for 22 hours. After the completion of the reaction, 590 ml of conc. hydrochloric acid were added thereto, and the solution was poured in 600 ml of methanol. Further, 25 ml of conc. hydrochloric acid were added thereto, and the solution was poured in 600 ml of methanol. Further, 25 ml of conc. hydrochloric acid were added thereto, and the mixture was heated at 50° C. for 1 hour. Then, the heating was stopped, and the reaction mixture was stirred for 3 hours. Crystals precipitated were filtered, washed well with methanol, and then dried at 50° C. under reduced pressure to give 17.4 g (55.5 mmols) as a white solid in a yield of 88.5%.

1H NMR (DMSO-d6): d 8.90 (s, 1H, H-8), 7.45–7.29 (m, 5H, Ph), 5.52 (s, 2H,Ph CH2); MS (ESI, MH+)=242.

Example 11

Acetic anhydride (4.44 ml, 45.1 mmols) and 132.8 mg (0.598 mmols) of p-toluenesulfonic acid monohydrate were added to a solution of 4.37 g (13.9 mmols) of 7-benzylguanine dihydrochloride in 9 ml of acetic acid. The mixture was reacted at 105° C. for 3 hours, and then allowed to cool. Water (180 ml) was poured into the reaction solution, and 150 ml of a 5-% sodium hydrogencarbonate aqueous solution and 100 ml of a 1-N sodium hydroxide aqueous solution were added thereto to adjust the pH to 5.3. Crystals were filtered, washed with 50 ml of water, and then dried at 55° C. for 5 hours under reduced pressure to obtain 3.77 g (13.3 mmols) of $N^2$-acetyl-7-benzylguanine as a white solid in a yield of 95.7%.

1H NMR (DMSO-d6): d 12.10 (brs, 1H), 11.57 (s, 1H), 8.35 (s, 1H, H-8), 7.41–7.25 (m, 5H, Ph), 5.51 (s, 2H, PhCH2), 2.16 (s, 3H, NHCOCH3).

Example 12

A solution of 473.3 mg (1.52 mmols, purity 91.2% by weight) of $N^2$-acetyl-7-benzylguanine in 2.2 ml of DMF was heated at 60° C. To this were added in small portions 483.0 mg (2.84 mmols) of 2,2-dimethyl- 1,3-dioxaspiro[5.2]octane-4,6-dione over a period of 12 hours, and the mixture was further heat-stirred at 60° C. for 12 hours. As the reaction proceeded, the solid was precipitated from the reaction solution which had been uniform immediately after starting the reaction. After the solid was allowed to cool to room temperature, 9.0 ml of ethyl acetate were added to the reaction solution to suspend the precipitated solid therein, and the solid was collected through filtration. This solid was dried at 50° C. under reduced pressure for 2 hours to give 562 mg of 5-[2-(2-acetylamino-7-benzylguanio-9-yl)ethyl]-2,2-dimethyl-1,3-dioxanecyclohexane-4,6-dionide as a light yellow solid in a yield of 81%.

1H NMR (DMSO-d6): d 9.62 (s, 1H), 7.51–7.32 (m, 5H), 5.64 (s, 2H), 4.20 (t, J=6.0 Hz, 2H), 2.64 (t, J=6.0 Hz, 2H), 2.21 (s, 3H), 1.35 (s, 6H); MASS (ESI MH+)=454.

Example 13

One hundred milligrams (0.22 mmols) of 5-[2-(2-acetylamino-7-benzylguanio-9-yl)ethyl]-2,2-dimethyl-1,3-dioxacyclohexane-4,6-dionide were suspended in 4.0 ml of a mixed solution of methanol and water [mixing ratio of 4:1 (v/v)]. To this were added 50.0 mg (0.011 mmols, water content 53.5%) of 5-% palladium on carbon as a catalyst, and the mixture was heat-stirred overnight at 60° C. and a normal pressure in a hydrogen atmosphere using a rubber balloon. After the reaction mixture as allowed to cool to room temperature, the catalyst was filtered through a Celite. The residue was washed with a mixed solution of methanol and water. This filtrate was concentrated, the white crystals formed were dissolved in 1.0 ml of a 2-N sodium hydroxide aqueous solution, and the resulting solution was stirred at 40° C. for 1.5 hours. After the temperature was returned to room temperature, the reaction mixture was neutralized to a pH of approximately 4 with 2-N hydrochloric acid. Then, the crystals were precipitated, and collected through filtration (primary crystals). The filtrate was concentrated, and a 2-N sodium hydroxide aqueous solution and 1-N hydrochloric acid were further added to the residue to adjust the pH to approximately 4. The crystals precipitated were collected through filtration (secondary crystals). These crystals were dried overnight at 50° C. under reduced pressure to give 56.9 mg of 9-(3,3-dicarboxypropa-1-yl)guanine white crystals as a combination of primary and secondary crystals in a yield of 92%.

1H NMR (DMSO-d6): d 10.51 (br s, 1H), 7.63 (s, 1H), 6.44(br s, 2H), 4.00 (t, J 7.6 Hz, 2H), 3.07–2.96 (m, 1H), 2.24–2.11 (m, 2H); 13C NMR (DMSO-d6): d 170.26, 156.76, 153.48, 151.14, 137.31, 116.54, 49.04, 40.94, 28.55; MASS (ESI MH+)=282.

Example 14

A solution of 710.0 mg (2.29 mmols, purity 91.2% by weight) of $N^2$-acetyl-7-benzylguanine in 10 ml of DMF was heated at 60° C. To this solution were added in small portions 724.5 mg (4.26 mmols) of 2,2-dimethyl-1,3-dioxaspiro[5.2]octane-4,6-dione over a period of 12 hours, and the mixture was further heat-stirred at 60° C. for 12 hours. As the reaction proceeded, the solid was precipitated from the reaction solution which had been uniform immediately after starting the reaction. After the reaction mixture was allowed to cool to room temperature, 50 ml of a mixed solution of methanol and water [mixing ratio of 4:1 (v/v)] were added thereto. To this were added 75.0 mg (0.017 mmols, water content 53.5%) of 5-% palladium on carbon as a catalyst, and the mixture was heat-stirred overnight at 60° C. and a normal pressure in a hydrogen atmosphere using a rubber balloon. After the reaction mixture was allowed to cool to room temperature, the catalyst was filtered through a Celite. The residue was washed with a mixed solution of methanol and water. This filtrate was concentrated, the white crystals formed were dissolved in a 2-N sodium hydroxide aqueous solution, and the resulting solution was stirred at 50° C. for 2 hours. After the temperature was returned to room temperature, the reaction mixture was neutralized to a pH of approximately 4 with 2-N hydrochloric acid. Then, the crystals precipitated were collected through filtration, and dried overnight at 50° C. under reduced pressure to give 500 mg of 9-(3,3-dicarboxypropa-1-yl)guanine white crystals in a yield of 77%.

1H NMR (DMSO-d6): d 10.51 (br s, 1H), 7.63 (s, 1H), 6.44 (br s, 2H), 4.00 (t, J=7.6 Hz, 2H), 3.07–2.96 (m, 1H), 2.24–2.11 (m, 2H); 13C NMR (DMSO-d6): d 170.26, 156.76, 153.48, 151.14, 137.31, 116.54, 49.04, 40.94, 28.55; MASS (ESI MH+)=282.

Obviously, numerous modifications and variations of the present invention are possible in light of the above teachings. It is therefore to be understood that within the scope of the appended claims, the invention may be practiced otherwise than as specifically described herein.

This application is based on Japanese Application No. 239031/1996, filed Sep. 10, 1996, and 282216/1996, filed Oct. 24, 1996. Both of these applications are incorporated herein by reference.

What is claimed as new and desired to be secured by Letters Patent of the Untied States is:

1. A process for producing a 7-benzylpurine derivative represented by formula (2), or a salt thereof:

(2)

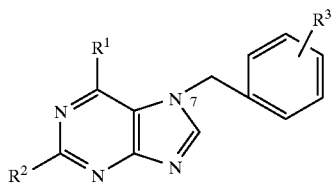

wherein $R^1$ is a hydrogen atom, a hydroxyl group, a $C_1$–$C_8$ alkoxy group, a $C_1$–$C_8$ saturated or unsaturated acyloxy group, a trialkyl siloxy group, a fluorine atom, a chlorine atom, a bromine atom, an iodine atom, an amino group, an amino group protected with one or two R'C(O) groups, a $C_1$–$C_{10}$ alkoxycarbonyl group, an aryloxycarbonylamino group, an unsubstituted benzyloxycarbonylamino group, a benzyloxycarbonylamino group, wherein said benzyloxycarbonylamino group is substituted with a $C_1$–$C_8$ alkyl group, a $C_1$–$C_8$ alkoxy group or a halogen atom or a $C_1$–$C_8$ alkyl group, R' is a $C_1$–$C_8$ alkyl group, $R^2$ is a hydrogen atom, a hydroxyl group, a $C_1$–$C_8$ alkoxy group, a $C_1$–$C_8$ saturated or unsaturated acyloxy group, a trialkyl siloxy group, a fluorine atom, a chlorine atom, a bromine atom, an iodine atom, an amino group, an amino group protected with one or two R'C(O) groups, wherein R' is as defined above, a $C_1$–$C_{10}$ alkoxycarbonyl group, an aryloxycarbonylamino group, an unsubstituted benzyloxycarbonylamino group, a benzyloxycarbonylamino group wherein said benzyloxycarbonylamino group is substituted with a $C_1$–$C_8$ alkyl group, a $C_1$–$C_8$ alkoxy group or a halogen atom or a $C_1$–$C_8$ alkyl group, and $R^3$ is a hydrogen atom, a $C_1$–$C_6$ alkyl group, a $C_1$–$C_6$ alkoxy group, a hydroxyl group, an amino group, a sulfonic acid group, a carboxy group, a $C_1$–$C_6$ alkoxycarbonyl group, a fluorine atom, a chlorine atom, a bromine atom, or an iodine atom, comprising benzylating the 7-position of an acetylpurine nucleoside represented by formula (1):

(1)

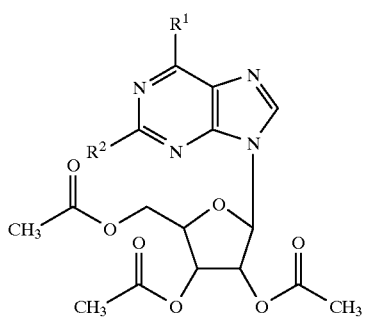

wherein $R^1$ and $R^2$ are as defined above, with a benzyl halide represented by formula (10):

(10)

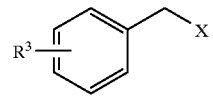

wherein

X is a halogen atom and $R^3$ is as defined above, and hydrolyzing the resultant product.

2. The process of claim 1, wherein $R^1$ is a hydroxyl group and $R^2$ is an amino group.

3. The process of claim 2, wherein $R^3$ is a hydrogen atom.

4. The process of claim 1, wherein $R^1$ is a hydroxyl group and $R^2$ is —NHCOCH$_3$.

5. The process of claim 4, wherein $R^3$ is a hydrogen atom.

6. The process of claim 1, wherein X is a bromine atom, an iodine atom or a chlorine atom.

7. The process of claim 1, wherein $R^3$ is a hydrogen atom.

8. The process of claim 1, wherein the 7-benzylpurine derivative is a salt of the acid used to hydrolyze the resultant product.

9. The process of claim 1, wherein a solution obtained by reacting an alkali salt of a purine nucleoside represented by formula (3)

(3)

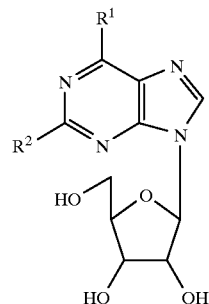

wherein $R^1$ and $R^2$ are as defined above, with acetic anhydride is used as the acetylpurine nucleoside of formula (1).

10. The process of claim 9, wherein the purine nucleoside of formula (3) is the sodium salt of guanosine.

11. A process for producing a 7-benzylpurine derivative represented by formula (2), or a salt thereof:

(2)

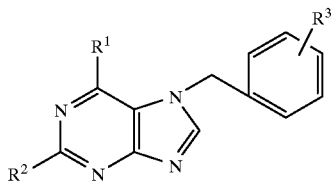

wherein $R^1$ is a hydrogen atom, a hydroxyl group, a $C_1$–$C_8$ alkoxy group, a $C_1$–$C_8$ saturated or unsaturated acyloxy group, a trialkyl siloxy group, a fluorine atom, a chlorine atom, a bromine atom, an iodine atom, an amino group, an amino group protected with one or two R'C(O) groups, a $C_1$–$C_{10}$ alkoxycarbonyl group, an aryloxycarbonylamino group, an unsubstituted benzyloxycarbonylamino group, a benzyloxycarbonylamino group, wherein said benzyloxycarbonylamino group is substituted with a $C_1$–$C_8$ alkyl group, a $C_1$–$C_8$ alkoxy group or a halogen atom or a $C_1$–$C_8$ alkyl group, R' is a $C_1$–$C_8$ alkyl group, $R^2$ is a hydroxyl group, a $C_1$–$C_8$ alkoxy group, a $C_1$–$C_8$ saturated or unsaturated acyloxy group, a trialkyl siloxy group, a fluorine atom, a chlorine atom, a bromine atom, an iodine atom, an amino group protected with one or two R'C(O) groups, wherein $R^1$ is as defined above, a $C_1$–$C_{10}$ alkoxycarbonyl group, an aryloxycarbonylamino group, an unsubstituted benzyloxycarbonylamino group, a benzyloxycarbonylamino group wherein said benzyloxycarbonylamino group is substituted with a $C_1$–$C_8$ alkyl group, a $C_1$–$C_8$ alkoxy group or a halogen atom or a $C_1$–$C_8$ alkyl group, and $R^3$ is a hydrogen atom, a $C_1$–$C_6$ alkyl group, a $C_1$–$C_6$ alkoxy group, a hydroxyl group, a nitro group, an amino group, a sulfonic acid group, a carboxy group, a $C_1$–$C_6$ alkoxycarbonyl group, a fluorine atom, a chlorine atom, a bromine atom, or an iodine atom, comprising benzylating the 7-position of an acetylpurine nucleoside represented by formula (1):

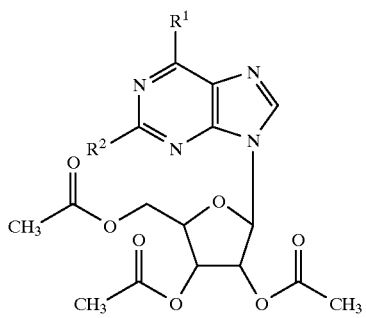

(1)

wherein $R^1$ and $R^2$ are as defined above, with a benzyl halide represented by formula (10):

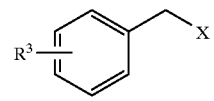

(10)

wherein

X is a halogen atom and $R^3$ is as defined above, and hydrolyzing the resultant product.

12. The process of claim 11, wherein $R^1$ is a hydroxyl group.

13. The process of claim 12, wherein $R^3$ is a hydrogen atom.

14. The process of claim 12, wherein $R^1$ is a hydroxyl group and $R^2$ is —NHCOCH$_3$.

15. The process of claim 14, wherein $R^3$ is a hydrogen atom.

16. The process of claim 12, wherein X is a bromine atom, an iodine atom or a chlorine atom.

17. The process of claim 12, wherein $R^3$ is a hydrogen atom.

18. The process of claim 12, wherein the 7-benzylpurine derivative is a salt of the acid used to hydrolyze the resultant product.

19. The process of claim 12, wherein a solution obtained by reacting an alkali salt of a purine nucleoside represented by formula (3)

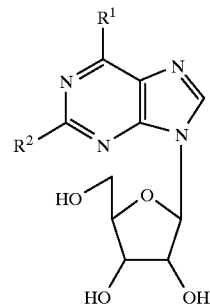

(3)

wherein $R^1$ and $R^2$ are as defined above, with acetic anhydride is used as the acetylpurine nucleoside of formula (1).

20. The process of claim 19, wherein the purine nucleoside of formula (3) is the sodium salt of guanosine.

* * * * *